(12) United States Patent
Jasra et al.

(10) Patent No.: US 7,294,745 B2
(45) Date of Patent: Nov. 13, 2007

(54) PROCESS FOR PREPARING ALDOL DERIVATIVES FROM ALKENES USING CATALYST

(75) Inventors: Raksh V. Jasra, Bhavnagar (IN); Vivek K. Srivastava, Bhavnagar (IN); Ram S. Shukla, Bhavnagar (IN); Hari C. Bajaj, Bhavnagar (IN); Sharad D. Bhatt, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 311 days.

(21) Appl. No.: 11/027,488

(22) Filed: Dec. 30, 2004

(65) Prior Publication Data

US 2006/0149101 A1    Jul. 6, 2006

(51) Int. Cl.
*C07C 45/50* (2006.01)
*C07C 45/72* (2006.01)

(52) U.S. Cl. ...................... 568/454; 568/463

(58) Field of Classification Search ............ 568/454, 568/463
See application file for complete search history.

(56) References Cited

U.S. PATENT DOCUMENTS

| | | | |
|---|---|---|---|
| 3,278,612 A | 10/1966 | Greene | |
| 3,821,311 A | 6/1974 | Hughes et al. | |
| 3,991,119 A | 11/1976 | Yoo | |
| 4,469,895 A | 9/1984 | Knifton et al. | |
| 5,144,089 A * | 9/1992 | Arena et al. | 568/463 |
| 5,254,743 A * | 10/1993 | Holmgren et al. | 568/463 |
| 5,334,770 A * | 8/1994 | Ueda et al. | 568/463 |
| 5,689,010 A | 11/1997 | Paciello et al. | |
| 5,756,856 A | 5/1998 | Bueschken et al. | |
| 6,307,093 B1 | 10/2001 | Godwin et al. | |
| 6,586,636 B2 * | 7/2003 | Kelly | 568/463 |

FOREIGN PATENT DOCUMENTS

EP    0 071 281 A2    2/1983

* cited by examiner

*Primary Examiner*—Sikarl A. Witherspoon
(74) *Attorney, Agent, or Firm*—Darby & Darby

(57) ABSTRACT

The present invention provides a novel eco-friendly multi-functional catalyst system useful to obtain $C_{2(n+1)}$ aldol-derivative from $C_n$-alkenes where n ranges from 2 to 10 in a single step under hydroformylation reaction conditions and adol formation conditions.

36 Claims, No Drawings

PROCESS FOR PREPARING ALDOL DERIVATIVES FROM ALKENES USING CATALYST

FIELD OF THE INVENTION

The present invention relates to a process for preparing aldol derivative from alkenes using a catalyst. More particularly, the present invention relates to preparation of $C_{2(n+1)}$ saturated and unsaturated aldol derivatives from $C_n$-alkenes, where n is 3, in a single step reaction using eco-friendly multi-functional catalyst system.

The present invention provides a process for preparing aldehydes of aldol derivatives having $C_6$-$C_{22}$ atoms by reacting alkenes having $C_2$-$C_{10}$ atoms with hydrogen and carbon monoxide under hydroformylation conditions in the presence of a multi-functional catalyst which comprises the metal complex hydridocarbonyltris(triphenylphosphine)rhodium(I) for hydroformylating the alkene, and a solid base such as magnesium-aluminum mixed oxides for aldolization of the aldehyde product of the said hydroformylation reaction in a single step.

BACKGROUND OF THE INVENTION

Aldehydes and alcohols containing one more carbon atom than a starting olefin can be prepared by transition metal-catalyzed reactions of the alkene with carbon monoxide and hydrogen. This reaction is known as hydroformylation or oxo reaction. Aldol condensation of aldehydes is a well-known reaction employed for many years in the production of several commercially important materials in addition to 2-ethylhexanol, for example, the formation of isophorone and mesitylene oxide from acetone. The reaction is not merely base catalyzed, but usually needs a strong base catalyst in order to proceed satisfactorily. Often the strong bases used as catalysts in aldol condensation are alkali metal hydroxides, especially under aqueous or partly aqueous conditions. Hence, it is well known that hydroformylation and aldol condensation are carried out as two separate processes.

Worldwide production and consumption of hydroformylation products (or oxo chemicals) exceeds 8.8 million metric tons per year. The applications of oxo products are in the manufacture of soaps, detergents and plastisizers. The largest share of almost 40% of total production capacity is covered by 2-ethylhexanol. Over 90% of world consumption of normal-butanal, which is synthesized from $C_n$-alkene where n is 3, is in a hydroformylation reaction where it is converted to 2-ethylhexanol and n-butanol while all detergent and $C_6$-$C_{13}$ plasticizer oxo aldehydes are converted to their corresponding alcohols. 2-Ethylhexanol, a valuable intermediate product for the chemical industry, is being used in the production of dioctyl phthalate, other plasticizers, coatings, adhesives and specialty chemicals. In these end use areas, it contributes significantly to many high performance characteristics such as flexibility, good adhesion, lower emissions and fuel performance improvement. Additionally, 2-ethylhexanol is oxidised to 2-ethylhexanol acid. This acid can also be manufactured by oxidation of 2-ethylhexanal produced by selective hydrogenation of 2-ethythexenal. 2-Ethylhexanoic acid is used for modifying alkyd resins while 2-ethylhexanal can also be used as a raw material for perfumes.

Commercially, butanal (both normal and iso) are initially produced by reaction of $C_n$-alkene, where n is 3, carbon monoxide and hydrogen namely hydroformylation or oxo reaction using organophosphine metal complex as a catalyst. Normal-butanal is separated from the product mixture by distillation process. The normal-butanal thus obtained from distillation process is subjected to condensation reaction namely aldol condensation reaction in presence of aqueous base lie KOH and NaOH etc. to give 2-ethylhexanal. The aldol condensation product, 2-ethylhexanal, is further subjected to hydrogenation reaction to get 2-ethylhexanol with use of appropriate catalytic of Nickel or Copper. The multi-steps involved in the production of 2-ethylhexanol from $C_n$-alkene, where n is 3, via hydroformylation, aldolization and hydrogenation is shown below:

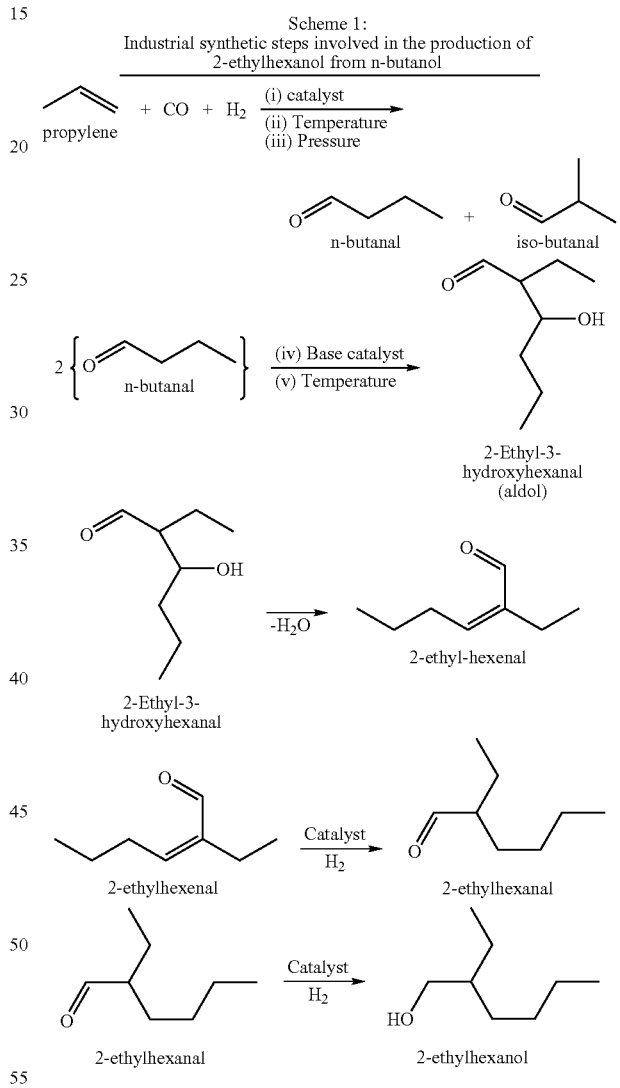

Scheme 1:
Industrial synthetic steps involved in the production of 2-ethylhexanol from n-butanol It has been estimated for the production of 2-ethylhexanol that approximately 25-30% of its selling price involves the cost of the product purification, recovery and waste treatment. The high capital expenses are also connected with the handling of strong liquid bases like KOH and/or NaOH during aldol condensation reaction. In addition to that, presently, about 1-1.5 tons of spent catalyst is being generated for every 10 tones production of 2-ethylhexanol. The industrial manufacture of 2-ethylhexanol involves very high capital cost since the synthetic strategy for production of 2-ethylhexanol (Scheme 1) has many drawbacks as written as (i) the synthetic strategy of 2-ethylhexanol from $C_n$-alkene, where n is 3, is a three step process is not economical from industrial and energy perspective. (ii) the use of hazardous reagents liquid KOH or NaOH in stoichiometric amount for aldol condensation in the second step and effluent problem in disposal of hazardous KOH(NaOH which is not eco-friendly route. (iii) the handling of liquid base KOH/NaOH and post synthesis work-up in separation of spent KOH or NaOH from reactants increases the capital cost of 2-ethylhexanol.

It is, therefore, highly desirable, to develop an eco-friendly multi-functional catalyst, which can reduce the multi-steps involved for the production of $C_{2(n+1)}$, saturated and unsaturated aldol-derivatives form C subs. n-alkenes, more specifically, production of 2-ethylhex-2-enal and/or 2-ethylhexanal and/or 2-ethylhexanol from $C_n$-alkene, where n is 3, in a single step. Many efforts are being carried out to accomplish the goal, some of them discussed in background of invention.

Reference is made to O. R. Hughes et al. U.S. Pat. No. 3,821,311 titled "Production of aldehyde from olefins" which describes a process related to production of aldehydes. More particularly this patent relates to production of $C_{2(n+1)}$ saturated and unsaturated aldehyde from $C_n$ terminal olefins. The main drawback is the use of hazardous aqueous base KOH for aldolization of aldehydes. The selectivity of $C_{2(n+1)}$ saturated and unsaturated aldehyde from $C_n$ terminal olefins is not more than 23%.

C. R. Greene et al. in U.S. Pat. No. 3,278,612 titled "Oxo process using cobalt carbonyl and tertiary phosphine under basic conditions" disclose a process for production of alcohols from organic compounds having less number of carbon atoms in the chain. More particularly the patent relates to production of $C_{n+1}$ and $C_{2(n+1)}$ alcohols from $C_n$ olefins such as butanol and 2-ethylhexanol simultaneously from $C_n$-alkene, where n is 3. The patent discloses catalytic synthesis of alcohols in presence of certain complex hydroformylation/hydrogenation catalysts in a particular reaction medium. The main drawback is the use of cobalt catalyst system for hydroformylation reaction, which is known to be inferior than rhodium and the use of hazardous amines and KOH for aldolization of aldehydes.

R. Paciello et al. in U.S. Pat. No. 5,689,010 titled "Preparation of higher aldehydes" disclose a process for preparing aldehydes with a higher number of carbon atoms and high selection by reacting olefins, in particular from petrochemical refinery products, by a hydroformylation with aldol condensation using a mixed catalyst of rhodium-carbonyl-phosphines and Mannich catalyst. The main drawback is use of Mannich catalyst for aldolization of aldehydes, since the catalyst is not eco-friendly.

J. F. Knifton et al in U.S. Pat. No. 4,469,895 titled "Process for preparing alcohols from olefins and synthesis gas" disclose an improved process of preparing predominantly linear alcohols by the steps of contacting a mixture of terminal and/or internal olefins and synthesis gas with a catalyst system comprising a ruthenium-containing compound in conjunction with one or more tertiary amine promoters, dispersed in a low melting quaternary phosphonium salt and heating said resultant reaction mixture under a pressure of 7 kg/cm² or greater at a temperature of at least 50° C. for a sufficient time to produce alcohols. The main drawback is that this process produces aldehyde and/or alcohols of $C_{n+1}$ carbon atom from $C_n$ olefins not aldehyde and/or alcohol of aldol derivatives $C_{2(n+1)}$ from olefins $C_n$ in hydroformylation conditions in single step. Moreover, the hydrogenation of aldehyde products to corresponding alcohols is a common feature under hydroformylation conditions.

J. S. Yoo in U.S. Pat. No. 3,991,119 titled "Hydroformylation over cobalt on support comprising separate alumina phase" discloses a new, solid catalyst suitable for the hydroformylation of low molecular weight olefins. The catalyst composition is a hydrido-cobalt or nickel carbonyl-Group VA electron donor ligand complex on a solid, acidic, silica-based support. Preferred electron donor ligands are phosphines and tertiary amines. A preferred catalyst support contains amorphous silica-alumina and alumina. The main drawback is the maximum Gas Chromatography (GC) % of 2-ethylhexanal obtained was less than 10% from $C_n$-alkene, where n is 3. Additionally, cobalt metal catalyst system that is inferior to rhodium metal system is used and the reaction condition and products yield are inferior. The solvent system is benzene, which is known to be a carcinogen. The catalyst system has not been used for other alkenes except $C_n$-alkene, where n is 3.

W. Bueschken et al. in U.S. Pat. No. 5,756,856 titled "Process for the preparation of 2-ethylhexanal" describes a process for the preparation of 2-ethylhexanal by catalytic hydrogenation of 2-ethylhex-2-enal, wherein the hydrogenation is carried out in a plurality of two or more series-connected loops, wherein each loop involves the use of one reactor, which comprises: (a) feeding 2-ethylhex-2-enal and hydrogen to an upper part of a reactor to catalytically hydrogenate said 2-ethylhex-2-enal to produce a hydrogenation product, (b) recycling a portion of said hydrogenation product back into said upper part of said reactor, (c) feeding the remainder of said hydrogenation product from said reactor to an upper part of a subsequent reactor wherein 2-ethylhex-2-enal is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 2-ethythex-enal from the product of step (e). The main drawback is 2-ethylhexanal is produced by catalytic hydrogenation of 2-ethylhex-2-enal and not from $C_n$-alkene, where n is 3, in single step.

OBJECTS OF THE INVENTION

The main object of the present invention is to provide a process for the preparation of aldol derivative from alkenes using catalyst, which obviate the drawbacks as detailed above.

Another object of the present invention is to provide a process for the preparation of production of 2-ethylhex-2-enal and/or 2-ethylhexanal and/or 2-ethylhexanol from C subs. n-alkene, where n is 3, in a single step reaction using eco-friendly multi-functional catalyst Still another object of the present invention is to provide a process to carry out the aldol condensation reaction without using hazardous liquid base.

Yet another object of the present invention is to provide a process for easy separation of products from the reaction mixture.

Yet another object of the present invention is to provide a process wherein effluent treatment of spent catalyst is reduced.

Yet another object of the present invention is to provide a process which comprise the re-usability of the catalytic system.

SUMMARY OF THE INVENTION

Accordingly the present invention provides a process for preparing an aldol derivative from the corresponding alkene in a single step system, the process comprising:

(a) contacting carbon monoxide and alkene with a catalyst system comprising hydridocarbonyltris(triphenylphosphine) rhodium(I) and a solid base in a solvent under hydroformylation and subsequently aldol condensation conditions to obtain a product stream;

(b) cooling product stream obtained in step (a) and separating aldol derivative so obtained.

In one embodiment of the invention, the alkene is a $C_n$ alkene where n is 3 and the product obtained is $C_{2(n+1)}$ aldol derivative.

In another embodiment of the invention, wherein the solvent is toluene.

In another embodiment of the invention, the solid base is a hydrotalcite.

In another embodiment of the invention, a metal complex hydridocarbonyltris(triphenylphosphine)rhodium(I) is contacted first with the solid base in toluene, degassed under inert atmosphere and the mixture stirred for 25 to 35 hours at a temperature in the range of 20 to 30° C., to impregnate the metal complex onto the base such that the magnesium to aluminum ratio in the base is in the range of 1.5 to 3.5.

In another embodiment of the invention, the base is hydrotalcite.

In yet another embodiment of the invention, the inert atmosphere is selected from nitrogen and argon.

In another embodiment of the invention the catalyst system is used in an amount in the range of 2 to 20 g/L with respect to solvent.

In another embodiment of the invention, the solvent is used in an amount of 0.02 to 0.07 liter.

In another embodiment of the invention, the impregnated catalyst system is introduced in an amount of 2 to 20 g/l into an autoclave containing the solvent in an amount of 0.02 to 0.07 liter, the autoclave heated till a temperature in the range of 50 to 300° C. is achieved and the temperature of the autoclave maintained in this temperature range.

In a further embodiment of the invention, gaseous $C_n$-alkene where n=3 is purged in the range of 0 to 5 kg/cm².

In a further embodiment of the invention, carbon monoxide and alkene is introduced into the autoclave to form a reaction mass and pressure is maintained in the range of 15 to 85 kg/cm² to facilitate hydroformylation and subsequently aldol condensation reactions.

In a further embodiment of the invention, the reaction mass is stirred for a period in the range of 10 to 25 hours, the supply of carbon monoxide and alkene stopped and a product aldol separated therefrom.

In another embodiment of the invention, the magnesium to aluminum molar ratio in the solid base is in the range of 2.0 to 3.5.

In another embodiment of the invention, the magnesium to aluminum molar ratio of the solid base in the catalyst is maintained at 2.0 and concentration of catalyst with respect to solvent is maintained in the range of 2 to 20 g/L.

In another embodiment of the invention, the magnesium to aluminum molar ratio of the solid base in the catalyst is maintained at 3.5 and concentration of the catalyst with respect to solvent is maintained in the range of 2 to 20 g/L.

In another embodiment of the invention, the magnesium to aluminum molar ratio of the solid base in the catalyst system is maintained at 3.5 and reaction pressure is maintained in the range of 20 to 90 kg/cm².

In another embodiment of the invention, the magnesium to aluminum molar ratio of the solid base in the catalyst is maintained at 2.0 and reaction temperature is maintained in the range of 50 to 300° C.

In another embodiment of the invention, the weight ratio of the metal complex to solid base is in the range of 1:35 to 1:70.

In another embodiment of the invention, the magnesium to aluminum molar ratio of the solid base in the catalyst system is maintained in the range 1.5 to 3.5.

In another embodiment of the invention, where n is in the range of 2 to 9.

In another embodiment of the invention, where n is 3 and weight ratio of the metal complex to solid base in the catalyst system is maintained at 1:35 and magnesium to aluminum molar ratio of the solid base in the catalyst is maintained at 3.5.

In another embodiment of the invention, n is 3 and the weight ratio of metal complex to solid base in the catalyst system is maintained at 1:35 and magnesium to aluminum molar ratio of the solid base in the catalyst is maintained at 3.5.

In another embodiment of the invention, n is 6, the weight ratio of the metal complex to solid base in the catalyst system is maintained at 1:35 and the magnesium to aluminum molar ratio of the solid base in the catalyst is maintained at 3.5.

In another embodiment of the invention, n is 9, weight ratio of the metal complex to solid base in the catalyst system is 1:35 and the magnesium to aluminum molar ratio of the solid base in the catalyst is maintained at 3.5.

In another embodiment of the invention, n is 10, weight ratio of the metal complex to solid base in the catalyst system is 1:35 and the magnesium to aluminum molar ratio of the solid base in the catalyst is maintained at 3.5.

In another embodiment of the invention, n is 3, weight ratio of the metal complex to solid base in the catalyst system is 1:35, the magnesium to aluminum molar ratio of the solid base in the catalyst is 1.5 and concentration of the catalyst with respect to solvent is maintained in the range of 2 to 30 g/L.

In another embodiment of the invention, n is 3, weight ratio of metal complex to solid base in the catalyst is 1:35, the magnesium to aluminum molar ratio of the solid base in the catalyst is 1.5 and the temperature is maintained in the range of 80 to 250° C.

In another embodiment of the invention, n is 3 and the magnesium to aluminum molar ratio of the solid base is in the range of 2.0 to 3.5.

In another embodiment of the invention, n is 3 and the reaction temperature is maintained in the range of 50° C. to 300° C.

In another embodiment of the invention, n is 3 and the reaction pressure is maintained in the range of 20 to 90 kg/cm².

In another embodiment of the invention n is in the range of 2 to 10 and the weight ratio of the metal complex and the solid base was in the range of 1:35 to 1:70.

In another embodiment of the invention, n is 3 and the magnesium to aluminum molar ratio in the solid base is selected from the group consisting of 1.5, 2.0, 2.5 and 3.5.

In another embodiment of the invention, n is 3 and 2 to 30 g/L of the catalyst system are used.

In another embodiment of the invention, n is 3 and the aldol reaction temperature is in the range of 80° C. to 250° C.

DETAILED DESCRIPTION OF THE INVENTION

Fundamental work by Wilkinson demonstrated that metal-organophosphine catalyst allowed operation of hydroformylation reaction of alkene at much lower pressure, which consequently leads to the hope of much lower capital and operating costs. The selectivity was also reported to be considerably higher; virtually no hydrogenation was observed and the linearity was in some cases as high as 90%. In addition to cobalt, which finds industrial use as a catalytic metal on a large scale, rhodium process has replaced many cobalt-based processes and known as Low Pressure Oxo (LPO) process. In the processes established in the art, the rhodium catalyst is generally a hydridorhodium carbonyl modified by additional ligands. A convenient catalyst precursor is hydridocarbonyl tris(tripbenylphosphine) rhodium (I). The hydroformylation reaction is generally run according to the aldehyde output.

Aldol condensation of aldehydes is a long-established reaction employed for many years in the production of several commercially important materials in addition to 2-ethylhexanol, for example, the formation of isophorone and mesitylene oxide from acetone. The reaction is not merely base catalyzed, but usually needs a strong base catalyst in order to proceed satisfactorily. Often the strong bases used as catalysts in aldol condensation are the alkali metal hydroxides, especially under aqueous or partly aqueous conditions. It should be apparent that the use of alkali metal hydroxides for the aldol condensation is having unfavorable environmental properties like the disposal of a hazardous strong base as well as the corrosion difficulties caused by a strong liquid base.

Magnesium-Aluminum mixed oxide is a clay with the ideal unit cell formula of $Mg_6 Al_2(OH)_{16}(CO_3)4H_2O$, and closely related analogs with variable magnesium/aluminum ratios may be readily prepared. Nakatsuka et al., Bull. Chem. Soc. Japan, 52, 2449 (1979) has described the catalytic use of "calcined synthetic hydrotalcite" with varying molar ratios of $MgO/Al_2O_3$ in batch mode polymerization of beta-propylactone. More extensive work was reported later on the use of "synthetic hydrotalcite" in various base-catalyzed reactions by W. T. Reichle, J. of Catalysis, 94, 547 (1985), who found that aldol condensations in a pulse reactor were readily catalyzed by "synthetic hydrotalcite" compositions having Mg/Al ratios from 1.3 to 6.3, although the Mg/Al ratio did not appear to have a significant effect on either its catalytic activity or efficiency. The structure, surface, and catalytic properties of magnesium-aluminum basic oxide has been studied in detail by C. R. Apsteguia et al., J. of Catalysis, 178, 499 (1998), who reported that the nature, density, and strength of surface basic sites on ex-magnesium-aluminum mixed oxide Magnesium-aluminum mixed oxides depend on the sample composition. In samples of low Al content, the basic site density is clearly lower as compared to pure MgO and on the other hand, higher Al contents increase the partial recovery of the basic site density. The study of activation of Magnesium-aluminum mixed oxide catalyst for aldol condensation reactions by F. Figueras et al., J. of Catalysis 173, 115, (1998), revealed that a good yield of aldol can indeed be obtained in heterogeneous catalysis using magnesium-aluminum mixed oxides, provided the solid is suitably activated and the reaction is performed at a low temperature and the aldolization is catalyzed by OH, as assumed in the classical organic mechanism. The structural requirement and reaction pathways in condensation reaction of alcohols on $Mg_yAlO_x$ catalysts has been reported by J. I. Di Cosimo et al., J. of Catalysis, 190, 261, (2000).

In the present invention, we report the synthesis of aldol derivatives $C_{2(n+1)}$ from their corresponding $C_n$ alkenes, more specifically 2-ethylhexanal and 2-etlylhexanol from $C_n$-alkene, where n is 3, in a single step in hydroformylation conditions using catalyst systems which comprises (i) the metal complex hydridocarbonyltris(triphenylphosphine)-rhodium(l) impregnated onto the surface of magnesium-aluminum mixed oxide and optionally, (ii) the weight ratio of the metal complex hydridocarbonyltris(triphenylphosphine)rhodium(l) and solid base (hydrotalcites) was varied in the range of 1:35 to 1:70.

The metal complex hydridocarbonyltris(triphenylphosphine)rhodium(I) is a highly preferred and commercially established catalyst precursor for efficient hydroformylation of alkenes more specifically $C_n$-alkene, where n is 3, to get highest linearity of corresponding aldehydes more specifically butanal in low pressure and low temperature conditions. Under ambient conditions, the catalyst precursor hydridocarbonyltris(triphenylphosphine)rhodium(I) slowly convert alkenes into expected aldehydes.

Layered double hydroxide materials, commonly known as Magnesium-aluminum mixed oxide like compounds or anionic clays are a family of natural and synthetic materials of general formula $M_x^{2+}M_y^{3+}(OH)_{2x+3y-nz}(A^{n-})_z \ldots mH_2O$. These materials are structurally similar to the mineral brucite, $Mg(OH)_2$, with a fraction of M(II) ions replaced by M(III) ions. This replacement results in a net positive charge on the octahedral layer, which is balanced by exchangeable interlayer anions. These materials are readily prepared by the addition of a base to solution containing a mixture of M(II) and M(III) ions. The naturally occurring counterpart of such structure, $Mg_6Al_2(OH)_{16}CO_34H_2O$ (hydrotalcites) contains trivalent $Al^{3+}$ cations located in the octahedral layer of $Mg(OH)_2$ while $CO_3^{2-}$ anions occupy the interlayer space to balance the net positive charge carried by trivalent $Al^{3+}$ cations. The use of double layer Magnesium-aluminum mixed oxide material for is highly studied base catalyst for aldol derivative from their corresponding alkenes more specifically 2-ethylhexanal and/or 2-ethylhexanol from butanal.

The synthesis of the catalyst precursor hydridocarbonyltris(triphenylphosphine) rhodium(I) and magnesium-aluminum mixed oxide of different magnesium to aluminum ratio and their impregnated catalyst system which will hereinafter be described in detail.

A solution of metal salt (M) (2.0 g, 7.6 mmol) in ethanol (70 ml) was added to a refluxing solution of ligand $EAr_3$ (12 g, 46.0 mmol) in ethanol (300 ml). After 2 minutes aqueous formaldehyde (10 ml) was added drop wise. Addition of sodiumborohydride, (2.0 g) in ethanol to this hot mixture yielded the crystals of hydridocarbonyltris(triphenylphosphine). rhodium(I). The yellow crystal was washed with ethanol.

Aqueous solution (0.22 L) containing nitrate salts of magnesium (0.223 mol) and aluminum (0.088 mol) for a ratio of Mg/Al=2.5, was added slowly to a second solution (0.221 L) containing sodium hydroxide (0.716 mol) and sodium carbonate (0.208 mol) in 1.0 L round bottom flask under vigorous stirring. The addition took nearly 3 h. The contents were then heated at 65° C. for 16 h. The precipitate formed was filtered and washed with hot distilled water until pH of the filtrate was 7. The precipitate dried in an oven at 80° C. for 15 h. The XRD patterns shows the presence of pure Magnesium-aluminum mixed oxide, with lattice parameter corresponding to those reported in the literature. The magnesium-aluminum mixed oxide of different magnesium to aluminum molar ratio have been synthesized according to above written procedure having proper moles of nitrate salts of magnesium and aluminum. The water used in all synthetic procedures was double distilled and deionized water.

The impregnated catalyst system was obtained by following method.

A 10 ml toluene solution of hydridocarbonyltris(triphenylphosphine)rhodium(I) appropriate quantity and triphenylphosphine of appropriate quantity was poured into a flask containing known amount of solid base (hydrotalcites) of different magnesium to aluminum molar ratio. After degassing, the mixture by vacuum boiling, argon (or nitrogen) was introduced and the slurry was stirred for 25 to 35 hours. Toluene was removed under vacuum at room temperature. The final product was a dry free-flowing light yellow powder, which was stored under inert atmosphere at the temperature range from 2° to 30° C.

The optionally used catalyst system was obtained by following method.

Complex hydridocarbonyltris(triphenylphosphine) rhodium(I) in appropriate quantity was mixed with the appropriate quantity of solid base (magnesium-aluminum mixed oxide) in order to obtain the weight ratio fro 1:3 5 to 1:70 at the temperature range from 21 to 30° C.

Characterization of catalyst precursor hydridocarbonyltris (triphenylphosphine) rhodium(I) was characterized by FT-NMR ($^1$H, $^{31}$P) and FT-IR spectroscopy by using Bruker Advance DPX 200 Mz FT-M and Perkin Elmer Spectrum GX FT-IR systems respectively. C, H, N elemental analysis was done on Perkin Elmer CHNS/O 2400 analyzer. The presence of bands at 2036 cm$^{-1}$ for ν (M—H) and 1936 cm$^{-1}$ for ν (C=O) in FT-IR confirmed the formation of rhodium complex hydridocarbonyltris(tiphenylphosphine) rhodium (I). Powder X-ray diffraction patterns of magnesium-aluminum mixed oxide were recorded with Phillips X'Pert MPD system equipped with XRK 900 reaction chamber, using Cu—Kα radiation (λ=1.54050 Å). Comparing the X-ray diffraction data with literature X-ray data checked the crystallinity of the adsorbent particles. The P-XRD pattern of magnesium-aluminum mixed oxides for each magnesium to aluminum molar ratio showed sharp and symmetric peaks at lower 2θ values, which were characteristics of hydrotalcites-like-compounds and the materials consisted of one phase only. The shoulders obtained at 1637, 1489 cm$^{-1}$ are the chrematistic bands of $CO_3^{2-}$ and $H_2O$ appeared in the FT-IR spectra of Magnesium-aluminum mixed oxide for each magnesium to aluminum molar ratio. BET surface area of magnesium-aluminum mixed oxide were determined by ASAP-2010C, Micromeritics, USA. The BET surface area of Magnesium-aluminum mixed oxide of magnesium to aluminum molar ratio of 1.5, 2.0, 2.5, 3.5 are 279.87 m$^2$/g, 276.69 m$^2$/g, 274.36 m$^2$/g, 271.98 m$^2$/g. The product analysis was carried out using Gas Chromatography (GC) (Shimadzu 17A, Japan), having 5% diphenyl and 95% dimethyl siloxane universal capillary column (60 m length and 0.32 mm diameter) and flame ionization detector (FID). The initial column temperature was increased from 40° C. to 200° C. at the-rate of 10° C./min. Nitrogen gas (3.4 ml/min) was used as a carrier gas. The temperature of injection port and Flame Ionization Detector (FID) were kept constant at 200° C. during product analysis. The retention times for different compounds were determined by injecting pure compounds under identical Gas Chromatography conditions. The following treatment of the raw data was used to derive the conversion and product distribution for the experiments.

% Conversion=(moles substrate reacted/moles substrate feed)×100%

Product Distribution:

% n-butanal=moles n-butanal/(moles of n-butanal+iso-butanal+n-butanol+iso-butanol+2-ethylhexenal+2-ethylhexanol)×100%

% iso-butanal=moles iso-butanal/(moles of n-butanal+iso-butanal+n-butanol+iso-butanol +2-ethythexenal+2-ethylhexanal+2-ethylhexanol)×100%

% n-butanol=moles n-butanol/(moles of n-butanal+iso-butanal+n-butanol+iso-butanol +2-ethylhexenal+2-ethylhexanal+2-ethylhexanol)×100%

% iso-butanol=moles iso-butanol/(moles of n-butanal+iso-butanal+n-butanol+iso-butanol +2-ethylhexenal+2-ethylhexanal+2-ethylhexanol)×100%

% 2-ethylhexenal=moles 2-ethylhexenal/(moles of n-butanal+iso-butanal+n-butanol+iso-butanol+2-ethylhexenal+2-ethylhexanal+2-ethylhexanol)×100%

% 2-ethylhexanal=moles 2-ethylhexanal/(moles of n-butanal+iso-butanal+n-butanol+iso-butanol+2-ethylhexenal+2-ethylhexanal+2-ethylhexanol)×100%

Gas Chromatography (GC), FT-NMR ($^1$H) and FT-IR spectroscopy to characterize the product mixture were also done by using Shimadzu 17A, Bruker Advance DPX 200NHz FT-NMR and Perkin Elmer Spectrum GX FT-IR systems, respectively. $^1$H-FT-NMR of the samples were done in $CDCl_3$ solvent from the range of 0 to 10 ppm.

All the experiments were carried out in 100 ml stainless steel autoclave reactor (Autoclave Engineers, U.S.A. Model No. E 01055A) equipped with a controlling unit. The reactor was kept in a fume cupboard under exhaust. The autoclave is designed with a three-gas liner; one for gas inlet, second for gas ventilation and third as a sampling valve. The autoclave is provided with propeller type stirrer. A pressure transducer monitor system with high precision (±2%) was connected to the reactor for online measurement of the pressure drop in the autoclave during the of reaction. The controlling unit can control the temperature (±0.50C) and speed of stirrer (±10 rpm). The propellers in the reactor are fixed at a position in which an improved gas distribution is observed leading to intensive gas-liquid contact with gas bubbles reacting at all parts of the liquid. The spraying of gases supplied inside the reactor is in such a way that sprayed gases covers all parts of the reactor.

The important inventive steps involved in the present invention are that the synthesis of eco-friendly multi-functional catalyst system, (i) is prepared by impregnation of said metal complex onto the surface of the said solid base like magnesium-aluminum mixed oxides (impregnated catalyst system), (ii) is prepared by uniformly mixing of the said metal complex hydridocarbonyltris(triphenylphosphine) rhodium(I) with the said solid base like magnesium-aluminum mixed oxides at room temperature (optionally used catalyst system) (iii) both the aforementioned types of catalyst system (1 and 2) were used for the single step synthesis of $C_{2(n+1)}$ aldol-derivatives from $C_n$-alkenes, where n ranges from 2 to 10.

The following examples are given by way of illustration and therefore should not be constructed to limit the scope of the present invention.

EXAMPLE-1

An impregnated catalyst system of magnesium to aluminum molar ratio 2.0 (2 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm. Reaction temperature was kept for 3 h at 50° C. After 3 h reaction temperature was raised to 150° C. from 50° C. to initiate aldolization. Reaction temperature was kept for 10 h at 150° C. temperature. Total reaction time was 13 h including hydroformylation and aldol condensation reactions. Meanwhile, reaction was continued at constant pressure by supplying CO and $H_2$ from the reservoir. After 13 h reaction time, the reaction was quenched. Autoclave was brought to room temperature with help of a cooling system and pressure drops were also noted. The orange-red solution of product mixture is then subjected to GC analysis. Product distribution was 10% for 2-ethylhexanal, 6% for 2-ethylhexenal, 60% for butanal with n/iso ratio 2.23 and 24% for butanol with n/iso ratio 3.14.

EXAMPLE-2

The impregnated catalyst system of magnesium to aluminum molar ratio 2.0 (10 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm. Reaction temperature was kept for 3 h at 50° C. After 3 h reaction temperature was raised to 150° C. from 50° C. to initiate aldolization. Reaction temperature was kept for 10 h at 150° C. temperature. Total reaction time was 13 h including hydroformylation and aldol condensation reactions. Meanwhile, the reaction was continued at constant pressure by supplying CO and $H_2$ from the reservoir. After 13 h reaction time, reaction was quenched. Autoclave was brought to room temperature with help of a cooling system and pressure drops were also noted. The orange-red solution of product mixture is then subjected to GC analysis. Product distribution was 41% for 2-ethylhexanal, 5% for 2-ethylhexenal, 45% for butanal with n/iso ratio 1.53 and 9% for butanol with n/iso ratio 3.12.

EXAMPLE-3

An impregnated catalyst system of magnesium to aluminum molar ratio 2.0 (20 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm. Reaction temperature was kept for 3 h at 50° C. temperature. After 3 h reaction temperature was raised to 150° C. from 50° C. to initiate aldolization reaction. Reaction temperature was kept for 10 h at 150° C. temperature. Total reaction time was 13 h including hydroformylation and aldol condensation reactions. Meanwhile, the reaction was continued at constant pressure by supplying CO and $H_2$ from reservoir. After 13 h reaction time, reaction was quenched. Autoclave was then brought to room temperature with help of a cooling system and pressure drops were also noted. The orange-red solution of product mixture is then subjected to GC analysis. Product distribution was 47% for 2-ethylhexanal, 13% for 2-ethylhexenal, 40% for butanal with n/iso ratio 1.02 and 0% for butanol.

EXAMPLE-4

An impregnated catalyst system of magnesium to aluminum molar ratio 2.0 (15 g/L) was charged in an autoclave containing 0.05 L toluene. Autoclave was flushed twice with nitrogen gas. Reactor was brought to 150° C. reaction temperature to conduct hydroformylation and aldolization reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm. Reaction temperature was kept at 150° C. temperature for 13 h. Meanwhile, the reaction was continued at constant pressure by supplying CO and $H_2$ from the reservoir. After 13 h reaction time, reaction was quenched. Autoclave was brought to room temperature with help of a cooling system and pressure drops were also noted. The orange-red solution of product mixture is then subjected to GC analysis. Product distribution was 52% for 2-ethylhexanal, 9% for 2-ethylhexenal, 39% for butanal with n/iso ratio 1.65 and 0% for butanol.

EXAMPLE-5

An impregnated catalyst system of magnesium to aluminum molar ratio 3.5 (2 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting stirrer at 1000 rpm. Reaction temperature was kept for 3 h at 50° C. After 3 h reaction temperature was raised to 150° C. from 50° C. to initiate aldolization. Reaction temperature was kept for 10 h at 150° C. temperature. Total reaction time was 13 h including hydroformylation and aldol condensation reactions. Meanwhile, the reaction was continued at constant pressure by supplying CO and $H_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 12% for 2-ethylhexanal, 5% for 2-ethylhexenal, 58% for butanal with n/iso ratio 2.13 and 25% for butanol with n/iso ratio 3.24.

EXAMPLE-6

An impregnated catalyst system of magnesium to aluminum molar ratio 3.5 (10 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm, Reaction temperature was kept for 3 h at 50° C. After 3 h reaction temperature was raised to 150° C. from 50° C. to initiate aldolization. Reaction temperature was kept for 10 h at 150° C. temperature. Total reaction time was 13 h including hydroformylation and aldol condensation reactions. Meanwhile, reaction was continued at constant pressure by supplying CO and $H_2$ from the reservoir. After 13 h reaction time, reaction was quenched. Autoclave was brought to room temperature with help of a cooling system and pressure drops were also noted. The orange-red solution of product mixture is then subjected to GC analysis. Product distribution was 43% for 2-ethylhexanal, 6% for 2-ethylhexenal, 45% for butanal with n/iso ratio 1.76 and 6% for butanol with n/iso ratio 2.99.

EXAMPLE-7

An impregnated catalyst system of magnesium to aluminum molar ratio 3.5 (20 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm, Reaction temperature was kept for 3 h at 50° C. temperature. After 3 h reaction temperature was raised to 150° C. from 50° C. to initiate aldolization. Reaction temperature was kept for 10 h at 150° C. temperature. Total reaction time was 13 h including hydroformylation and aldol condensation reactions, Meanwhile, the reaction was continued at constant pressure by supplying CO and $H_2$ from reservoir vessel. After 13 h reaction time, reaction was quenched. Autoclave was brought to room temperature with help of a cooling system and pressure drops were also noted. The orange-red solution of the product mixture is then subjected to GC analysis. The product distribution was 48% for 2-ethylhexanal, 13% for 2-ethylhexenal, 39% for butanal with n/iso ratio 1.12 and 0% for butanol.

EXAMPLE-8

An impregnated catalyst system of magnesium to aluminum molar ratio 3.5 (15 g/L) was charged in an autoclave containing 0.05 L toluene. Autoclave was flushed twice with nitrogen gas, Reactor was then brought to 150° C. reaction temperature to conduct hydroformylation and aldolization reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rotation per minute (rpm). Reaction temperature was kept at 150° C. temperature for 13 h. Meanwhile, the reaction was continued at constant pressure by supplying CO and $H_2$ from reservoir vessel. After 13 h reaction time, the reaction was quenched. The autoclave was brought to room temperature with the help of a cooling system and pressure drops were also noted. The orange-red solution of the product mixture was then subjected to GC analysis. Product distribution was 54% for 2-ethylhexanal, 6% for 2-ethylhexenal, 40% for butanal with n/iso ratio 1.55 and 0% for butanol.

EXAMPLE-9

An impregnated catalyst system of magnesium to aluminum molar ratio 3.5 (10 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (2 kg/cm$^2$) and hydrogen $H_2$ (8 kg/cm$^2$) from reservoir. Reaction was initiated by starting the stirrer at 1000 rpm. Reaction temperature was kept for 3 h at 50° C. temperature. After 3 h reaction temperature was raised to 150° C. from 50° C. to initiate aldolization. Reaction temperature was kept for 10 h at 150° C. temperature. Total reaction time was 13 h including hydroformylation and aldol condensation reactions. Meanwhile, reaction was continued at constant pressure, by supplying CO and $H_2$ from the reservoir. After 13 h reaction time, reaction was quenched. Autoclave was brought to room temperature with help of a cooling system and pressure drops were also noted. The orange-red solution of product mixture is then subjected to GC analysis. Product distribution was 38% for 2-ethylhexanal, 12% for 2-ethylhexenal, 42% for butanal with n/iso ratio 1.19 and 8% for butanol with n/iso ratio 2.27.

EXAMPLE-10

An impregnated catalyst system of magnesium to aluminum molar ratio 3.5 (10 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (20 kg/cm$^2$) and hydrogen $H_2$ (60 kg/cm$^2$) from reservoir. Reaction was initiated by starting the stirrer at 1000 rpm. Reaction temperature was kept for 3 h at 50° C. temperature. After 3 h reaction temperature was raised to 150° C. from 50° C. to initiate aldolization. Reaction temperature was kept for 10 h at 150° C. temperature. Total reaction time was 13 h including hydroformylation and aldol condensation reactions. Meanwhile, reaction was continued at constant pressure by supplying CO and $H_2$ from the reservoir, After 13 h reaction time, reaction was quenched. Autoclave was brought to room temperature with help of a cooling system and pressure drops were also noted. The orange-red solution of product mixture is then subjected to GC analysis. Product distribution was 47% for 2-ethylhexanal, 9% for 2-ethylhexenal, 31% for butanal with n/iso ratio 1.71 and 13% for butanol with n/iso ratio 3.96.

EXAMPLE-11

An impregnated catalyst system of magnesium to aluminum molar ratio 2.0.(10 g/L) was charged in an autoclave containing 0.05 L toluene. Autoclave was flushed twice with nitrogen gas. Reactor was then brought to 50° C. reaction temperature to conduct hydroformylation and aldolization reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. The reaction was then initiated by starting the stirrer at 1000 rotation per minute (rpm). The total reaction time was 13 h. Meanwhile, the reaction was continued at constant pressure, by supplying CO and $H_2$ from the reservoir vessel. After 13 h reaction time, the reaction was quenched. The autoclave was then brought to room temperature with the help of a cooling system and the pressure drops were also noted. The orange-red solution of the product mixture is then subjected to GC analysis. Product distribution was 12% for 2-ethylhexanal, 0% for 2-ethylhexenal, 83% for butanal with n/iso ratio 1.65 and 5% for butanol.

EXAMPLE-12

An impregnated catalyst system of magnesium to aluminum molar ratio 2.0 (10 g/L) was charged in an autoclave containing 0.05 L toluene. Autoclave was flushed twice with nitrogen gas. Reactor was brought to 150° C. reaction temperature to conduct hydroformylation and aldolization reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. The reaction was then initiated by starting the stirrer at 1000 rotation per minute (rpm). The total reaction time was 13 h. Meanwhile, the reaction was continued at constant pressure, by supplying CO and $H_2$ from the reservoir vessel. After 13 h reaction time, the reaction was quenched. The autoclave was then brought to room temperature with the help of a cooling system and the pressure drops were also noted. The orange-red solution of the product mixture is then subjected to GC analysis. Product distribution was 48% for 2-ethylhexanal, 20% for 2-ethylhexenal, 30% for butanal with n/iso ratio 1.19 and 2% for butanol.

EXAMPLE-13

An impregnated catalyst system of magnesium to aluminum molar ratio 2.0 (10 g/L) was charged in an autoclave containing 0.05 L toluene. Autoclave was flushed twice with nitrogen gas. Reactor was brought to 300° C. reaction temperature to conduct hydroformylation and aldolization reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. The reaction was then initiated by starting the stirrer at 1000 rotation per minute (rpm). The total reaction time was 13 h. Meanwhile, the reaction was continued at constant pressure, by supplying CO and $H_2$ from the reservoir vessel. After 13 h reaction time, the reaction was quenched. The autoclave was then brought to room temperature with the help of a cooling system and the pressure drops were also noted. The orange-red solution of the product mixture is then subjected to GC analysis. Product distribution was 51% for 2-ethylhexanal, 0% for 2-ethylhexenal, 0% for butanal and 49% for butanol with n/iso ratio 1.61

EXAMPLE-14

An optionally used catalyst system of magnesium to aluminum molar ratio 3.5 (15 g/L) was charged in an autoclave containing 0.05 L toluene. Autoclave was flushed twice with nitrogen gas. Reactor was brought to reaction temperature 50° C. to conduct hydroformylation reaction prior to introducing mixture of $C_n$-alkene (n=2) (10 kg/cm$^2$), carbon monoxide CO (5 kg/cm$^2$), and hydrogen $H_2$ (15 kg/cm$^2$) from reservoir. The reaction was then initiated by starting the stirrer at 1000 rotation per minute (rpm). The reaction temperature kept for 3 h at 50° C. temperature. After 3 h the reaction temperature was raised to 150° C. from 50° C. to initiate aldolization (aldol condensation) reaction. The reaction temperature kept for 10 h at 150° C. temperature. Hence, the total reaction time was 13 h including hydroformylation and aldol condensation reactions. Meanwhile, the reaction was continued at constant pressure, by supplying CO and $H_2$ from the reservoir vessel. After 13 h reaction time, the reaction was quenched. The autoclave was then brought to room temperature with the help of a cooling system and the pressure drops were also noted. The orange-red solution of the product mixture is then subjected to GC analysis. Product distribution was 87% for aldol product $C_{2(n+1)}$, 13% for oxo product $C_{n+1}$ aldehydes.

EXAMPLE-15

A catalyst system of magnesium to aluminum molar ratio 3.5 (15 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rotation per minute (rpm). Reaction temperature was kept for 3 h at 50° C. temperature. After 3 h the reaction temperature was raised to 150° C. from 50° C. to initiate aldolization (aldol condensation) reaction. Reaction temperature was kept for 10 h at 150° C. temperature. Total reaction time was 13 h including hydroformylation and, aldol condensation reactions. Meanwhile, reaction was continued at constant pressure by supplying CO and $H_2$ from the reservoir vessel. After 13 h reaction time, the reaction was quenched. Autoclave was then brought to room temperature with the help of a cooling system and the pressure drops were also noted. The orange-red solution of product mixture is then subjected to GOC analysis. Product distribution was 72% for aldol product $C_{2(n+1)}$, 28% for oxo product $C_{n+1}$ aldehydes.

EXAMPLE-16

A catalyst system of magnesium to aluminum molar ratio 3.5 (15 g/L) and $C_n$-alkene (n=6) (2.0 g) was charged in an autoclave containing 0.05 L toluene. Autoclave was flushed twice with nitrogen gas. Reactor was brought to 50° C. reaction temperature to conduct hydroformylation reaction prior to successively introducing mixture of carbon monoxide CO (5 kg/cm$^2$) and hydrogen $H_2$ (15 kg/cm$^2$) from reservoir. Reaction was initiated by starting the stirrer at 1000 rotation per minute (rpm). Reaction temperature was kept for 3 h at 50° C. temperature. After 3 h reaction temperature was raised to 150° C. from 50° C. to initiate aldolization (aldol condensation) reaction. Reaction temperature was kept for 10 h at 150° C. temperature. Total reaction time was 13 h including hydroformylation and aldol condensation reactions. Meanwhile, the reaction was continued at constant pressure, by supplying CO and $H_2$ from the reservoir vessel. After 13 h reaction time, the reaction was quenched. Autoclave was then brought to room temperature with the help of a cooling system and pressure drops were also noted. The orange-red solution of product mixture is then subjected to GC analysis. Product distribution was 44% for aldol product $C_{2(n+1)}$, 16% for oxo product $C_{n+1}$ aldehydes and 40% for isomerization and hydrogenation of $C_n$ alkene.

EXAMPLE-17

A catalyst system of magnesium to aluminum molar ratio 3.5 (15 g/L) and $C_n$-alkene (n=9) (2.0 g) was charged in an autoclave containing 0.05 L toluene. Autoclave was flushed twice with nitrogen gas. Reactor was brought to 50° C. reaction temperature to conduct hydroformylation reaction prior to successively introducing mixture of carbon monoxide CO (5 kg/cm$^2$) and hydrogen H$_2$ (15 kg/cm) from reservoir. Reaction was initiated by starting the stirrer at 1000 rotation per minute (rpm). Reaction temperature was kept for 3 h at 50° C. temperature. After 3 h reaction temperature was raised to 150° C. from 50° C. to initiate aldolization (aldol condensation) reaction. Reaction temperature was kept for 10 h at 150° C. temperature. Total reaction time was 13 h including hydroformylation and aldol condensation reactions. Meanwhile, the reaction was continued at constant pressure by supplying CO and H$_2$ from the reservoir vessel. After 13 h reaction time, the reaction was quenched. Autoclave was brought to room temperature with the help of a cooling system and pressure drops were also noted. The orange-red solution of product mixture is then subjected to GC analysis. The product distribution was 18% for aldol product C$_{2(n+1)}$, 64% for oxo product C$_{n+1}$ aldehydes and 18% for isomerization and hydrogenation of C$_n$ alkene.

EXAMPLE-18

A catalyst system of magnesium to aluminum molar ratio 3.5 (15 g/L) and C$_n$-alkene (n=10) (2.0 g) was charged in an autoclave containing 0.05 L toluene. Autoclave was flushed twice with nitrogen gas. Reactor was brought to 50° C. reaction temperature to conduct hydroformylation reaction prior to successively introducing mixture of carbon monoxide CO (5 kg/cm$^2$) and hydrogen H$_2$ (15 kg/cm$^2$) from reservoir. Reactor was then brought to 50° C. reaction temperature for initiating hydroformylation reaction. Reaction was initiated by starting the stirrer at 1000 rotation per minute (rpm). Reaction temperature was kept for 3 h at 50° C. temperature. After 3 h reaction temperature was raised to 150° C. from 50° C. to initiate aldolization (aldol condensation) reaction. Reaction temperature was kept for 10 h at 150° C. temperature. Total reaction time was 13 h including hydroformylation and aldol condensation reactions. Meanwhile, the reaction was continued at constant pressure, by supplying CO and H$_2$ from the reservoir vessel. After 13 h reaction time, the reaction was quenched. Autoclave was then brought to room temperature with the help of a cooling system and the pressure drops were also noted. The orange-red solution of the product mixture is then subjected to GC analysis. The product distribution was, 7% for aldol product C$_{2(n+1)}$, 84% for oxo product C$_{n+1}$ aldehydes and 9% for isomerization and hydrogenation of C$_n$ alkene.

EXAMPLE-19

A catalyst system of magnesium to aluminum molar ratio 1.5 (15 g/L) was charged in an autoclave containing 0.05 L toluene. Autoclave was flushed twice with nitrogen gas. Reactor was brought to 50° C. reaction temperature to conduct hydroformylation reaction prior to introducing mixture of C$_n$-alkene (n=3) (10 kg/cm$^2$), carbon monoxide CO (5 kg/cm$^2$) and hydrogen H$_2$ (15 kg/cm$^2$) from reservoir. Reaction was initiated by starting the stirrer at 1000 rpm. Reaction temperature was kept for 3 h at 50° C. temperature. After 3 h reaction temperature was raised to 150° C. from 50° C. to initiate aldolization reaction. Reaction temperature was kept for 10 h at 150° C. temperature. Total reaction time was 13 h including hydroformylation and aldol condensation reactions, Meanwhile, reaction was continued at constant pressure by supplying CO and H$_2$ from the reservoir vessel. After 13 h reaction time, the reaction was quenched. Autoclave was then brought to room temperature with help of a cooling system and pressure drops were also noted. The orange-red solution of product mixture is then subjected to GC analysis. Product distribution was 38% for 2-ethylhexanal, 22% for 2-ethylhexenal, 40% for butanal with n/iso ratio 0.86 and 0% for butanol.

EXAMPLE-20

A catalyst system of magnesium to aluminum molar ratio 3.5 (15 g/L) was charged in an autoclave containing 0.05 L toluene. Autoclave was flushed twice with nitrogen gas. Reactor was brought to 50° C. reaction temperature to conduct hydroformylation reaction prior to introducing mixture of C$_n$-alkene (n=3) (10 kg/cm$^2$), carbon monoxide CO (5 kg/cm$^2$) and hydrogen H$_2$ (15 kg/cm ) from reservoir. Reaction was initiated by starting the stirrer at 1000 rpm. Reaction temperature was kept for 3 h at 50° C. After 3 h, the reaction temperature was raised to 150° C. from 50° C. to initiate aldolization reaction. Reaction temperature was kept for 10 h at 150° C. Total reaction time was 13 h including hydroformylation and aldol condensation reactions. Meanwhile, the reaction was continued at constant pressure by supplying CO and H$_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 59% for 2-ethylhexanal, 12% for 2-ethylhexenal, 29% for butanal with n/iso ratio 0.82 and 0% for butanol.

EXAMPLE-21

A catalyst system of magnesium to aluminum molar ratio 1.5 (2 g/L) was charged in an autoclave containing 0.05 L toluene. Autoclave was flushed twice with nitrogen gas. Reactor was brought to 50° C. reaction temperature to conduct hydroformylation reaction prior to introducing mixture of C$_n$-alkene (n=3) (10 kg/cm$^2$), carbon monoxide CO (5 kg/cm$^2$) and hydrogen H$_2$ (15 kg/cm$^2$) from reservoir. Reaction was initiated by starting stirrer at 1000 rpm. Reaction temperature was kept for 3 h at 50° C. After 3 h, reaction temperature was raised to 150° C. from 50° C. to initiate aldolization. Reaction temperature was kept for 10 h at 150° C. Total reaction time was 13 h including hydroformylation and aldol condensation reactions. Meanwhile, reaction was continued at constant pressure by supplying CO and H$_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 8% for 2-ethylhexanal, 6% for 2-ethylhexenal, 65% for butanal with n/iso ratio 1.36 and 21% for butanol with n/iso ratio 1.78.

EXAMPLE-22

A catalyst system of magnesium to aluminum molar ratio 1.5 (10 g/L) was charged in an autoclave containing 0.05 L toluene. Autoclave was flushed twice with nitrogen gas. Reactor was brought to 50° C. reaction temperature to conduct hydroformylation reaction prior to introducing mixture of C$_n$-alkene (n=3) (10 kg/cm$^2$), carbon monoxide CO (5 kg/cm$^2$) and hydrogen H$_2$ (15 kg/cm) from reservoir. Reaction was initiated by starting the stirrer at 1000 rpm. Reaction temperature was kept for 3 h at 50° C. After 3 h, reaction temperature was raised to 150° C. from 50° C. to initiate aldolization. Reaction temperature was kept for 10 h at 150° C. Total reaction time was 13 h including hydroformylation and aldol condensation reactions. Meanwhile, the reaction was continued at constant pressure by supplying CO and $H_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 30% for 2-ethylhexanal, 18% for 2-ethylhexenal, 46% for butanal with n/iso ratio 1.08% and 6% for normal-butanol.

EXAMPLE-23

A catalyst system of magnesium to aluminum molar ratio 1.5 (30 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm. Reaction temperature was kept for 3 h at 50° C. After 3 h, reaction temperature was raised to 150° C. from 50° C. to initiate aldolization. Reaction temperature was kept for 10 h at 150° C. Total reaction time was 13 h including hydroformylation and aldol condensation reactions. Meanwhile, the reaction was continued at constant pressure by supplying CO and $H_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 39% for 2-ethylhexanal, 23% for 2-ethylhexenal, 34% for butanal with n/iso ratio 0.65 and 4% for normal-butanol.

EXAMPLE-24

A catalyst system of magnesium to aluminum molar ratio 1.5 (15 g/L) was charged in an autoclave containing 0.05 L toluene, Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm ) and hydrogen $H_2$ (15 kg/cm$^2$) from reservoir. Reaction was then initiated by starting the stirrer at 1000 rpm. Reaction temperature was kept for 3 h at 50° C. After 3 h, reaction temperature was raised to 80° C. from 50° C. to initiate aldolization. Reaction temperature was kept for 10 h at 80° C. Total reaction time was 13 h including hydroformylation and aldol condensation reactions. Meanwhile, reaction was continued at constant pressure by supplying CO and $H_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 12% for 2-ethylhexanal, 0% for 2-ethylhexenal, 70% for butanal with n/iso ratio 1.68 and 18% for butanol with n/iso ratio 1.56.

EXAMPLE-25

A catalyst system of magnesium to aluminum molar ratio 1.5 (15 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting stirrer at 1000 rpm. Reaction temperature was kept for 3 h at 50° C. After 3 h reaction temperature was raised to 175° C. from 50° C. to initiate aldolization. Reaction temperature was kept for 10 h at 175° C. Total reaction time was 13 h including hydroformylation and aldol condensation reactions. The reaction was continued at constant pressure by supplying CO and $H_2$ from the reservoir. After 13 h reaction time, reaction was quenched. Autoclave was brought to room temperature with help of a cooling system and pressure drops were also noted. Orange-red solution of product mixture was subjected to GC analysis. Product distribution was 42% for 2-ethylhexanal, 29% for 2-ethylhexenal, 29% for butanal with n/iso ratio 0.87 and 0% for butanol.

EXAMPLE-26

A catalyst system of magnesium to aluminum molar ratio 1.5 (15 g/L) was charged in an autoclave containing 0.05 L toluene. Autoclave was flushed twice with nitrogen gas. Reactor was brought to 50° C. reaction temperature to conduct hydroformylation reaction prior to introducing mixture of $C_n$-alkene (n=3) (10 kg/cm$^2$), carbon monoxide CO (5 kg/cm$^2$) and hydrogen $H_2$ (15 kg/cm$^2$) from reservoir. Reaction was initiated by starting the stirrer at 1000 rpm. Reaction temperature was kept for 3 h at 50° C. After 3 h, reaction temperature was raised to 250° C. from 50° C. to initiate aldolization. Reaction temperature was kept for 10 h at 250° C. Total reaction time was 13 h including hydroformylation and aldol condensation reactions. Meanwhile, the reaction was continued at constant pressure by supplying CO and $H_2$ from the reservoir. After 13 h reaction time, reaction was quenched. Autoclave was then brought to room temperature with help of a cooling system and pressure drops were also noted. The orange-red solution of product mixture is then subjected to GC analysis. Product distribution was 9% for 2-ethylhexanal, 50% for 2-ethylhexenal, 23% for butanal with n/iso ratio 0.74 and 18% for butanol with n/iso ratio 0.89.

The Main Advantages of the Present Invention Include:
1. Preparation of $C_{2(n+1)}$ saturated and unsaturated aldol product from $C_n$ alkene, more specifically, 2-ethythexenal and/or 2-ethylhexenal from $C_n$ alkene (n=3) in a single reaction under hydroformylation reaction conditions using eco-friendly multi-functional catalytic system.
2. Substitution of eco-friendly solid bases (magnesium-aluminum mixed oxide) in place of hazardous liquid bases like KOH and/or NaOH for aldolization of hydroformylation products.
3. Reduction of multi-steps involved in production $C_{2(n+1)}$ saturated and unsaturated aldehyde from $C_n$ alkene by a single step reaction.
4. Reduction of high capital costs involved in the handling of liquid bases like KOH and/or NaOH during aldolization reactions.
5. Reduction of effluent problem in disposal of hazardous liquid bases like KOH and/or NaOH after aldolization reaction.
6. Maximum selectivity $C_{2(n+1)}$ saturated and unsaturated aldehyde from $C_n$ alkene found using non-carcinogenic solvent toluene in place of carcinogenic solvent benzene.

7. Selectivity of $C_{2(n+1)}$ saturated and unsaturated aldehyde from $C_n$ alkene (n=2) found upto 87%, which is maximum with any catalytic system reported so far.
8. Selectivity of $C_{2(n+1)}$ saturated and unsaturated aldehyde from $C_n$ alkene (n=3) found more than 70%, which is maximum with any catalytic system reported so far.
9. Selectivity of $C_{2(n+1)}$ saturated and unsaturated aldehyde from $C_n$ alkene (n=3) found more than 70% using eco-friendly multifunctional catalytic system, which is maximum with any hazardous and/or non-hazardous catalytic system reported so far.

We claim:

1. Process for preparing an aldol derivative from the corresponding alkene in a single step using a eco-friendly multi-functional catalyst system, the process comprising:
   (a) contacting carbon monoxide, hydrogen and an alkene with a catalyst system consisting of a metal complex comprising hydridocarbonyltris(triphenylphosphine)rhodium(I) and a solid base, in a solvent under hydroformylation and subsequently aldol condensation conditions to obtain a product stream;
   (b) cooling the product stream obtained in step (a) and separating the aldol derivative so obtained, wherein the hydridocarbonyltris(triphenylphosphine) rhodium(I) is contacted first with the solid base and degassed under an inert atmosphere and the mixture stirred for 25 to 35 hours at a temperature in the range of 20 to 30° C. to impregnate the metal complex onto the base such that the magnesium to aluminum ratio in the base is in the range of 1.5 to 3.5.

2. Process as claimed in claim 1 wherein the alkene is a $C_n$ alkene and the product obtained is $C_{2(n+1)}$ aldol derivative, where n in the alkene and the product aldol is in the range of 2 to 10.

3. Process as claimed in claim 1 wherein the solvent is toluene.

4. Process as claimed in claim 1 wherein the solid base is a hydrotalcite.

5. Process as claimed in claim 1 wherein the hydridocarbonyltris(triphenylphosphine) rhodium(I) is contacted with the solid base in toluene.

6. Process as claimed in claim 5 wherein the base is hydrotalcite.

7. Process as claimed in claim 1 wherein the inert atmosphere is selected from nitrogen and argon.

8. Process as claimed in claim 1 wherein the catalyst system is used in an amount in the range of 2 to 20 g/L with respect to solvent.

9. Process as claimed in claim 1 wherein the solvent is used in an amount of 0.02 to 0.07 L.

10. Process as claimed in claim 1 wherein the impregnated catalyst system is introduced in an amount of 2 to 20 g/l into an autoclave containing the solvent in an amount of 0.02 to 0.07 liter, the autoclave heated till a temperature in the range of 50 to 300° C. is achieved and the temperature of the autoclave maintained in this temperature range.

11. Process as claimed in claim 1 wherein gaseous $C_n$-alkene where n=3 is purged in the range of 0 to 5 kg/cm².

12. Process as claimed in claim 1 wherein carbon monoxide and the alkene is introduced into the autoclave to form a reaction mass and pressure is maintained in the range of 15 to 85 kg/cm² to facilitate hydroformylation and subsequently aldol condensation reactions.

13. Process as claimed in claim 12 wherein the reaction mass is stirred for a period in the range of 10 to 25 hours, the supply of carbon monoxide and alkene stopped and a product aldol separated therefrom.

14. Process as claimed in claim 1 wherein the magnesium to aluminum molar ratio in the solid base is in the range of 2.0 to 3.5.

15. Process as claimed in claim 1 wherein the process comprises:
   (i) treating the metal complex hydridocarbonyltris(triphenylphosphine)rhodium(I) in toluene with the solid base, degassing under inert atmosphere selected from nitrogen and argon and stirring for 25 to 35 hours at temperature in the range of 20 to 30° C. such that the impregnated catalyst containing the solid base had the magnesium to aluminum molar ratio in the range of 2.0 and 3.5;
   (ii) adding impregnated catalyst system in the range of 2 to 20 g/L into an autoclave containing 0.02 to 0.07 liter toluene as solvent;
   (iii) heating the autoclave containing the solvent and catalyst system and maintaining temperature in the range of 50 to 300° C.;
   (iv) purging gaseous $C_n$-alkene where n=3 in the range of 0 to 5 kg/cm²;
   (v) introducing carbon monoxide and hydrogen gases into autoclave and maintaining pressure in the range of 15 to 85 kg/cm² to facilitate hydroformylation and subsequently aldol condensation reactions;
   (vi) stirring the reaction mass and maintaining it in the range of 10 to 25 hours;
   (vii) quenching the reaction by stopping gas supply to the autoclave;
   (viii) separating the reaction products from the reactant.

16. Process as claimed in claim 1 wherein the magnesium to aluminum molar ratio of the solid base in the catalyst is maintained at 2.0 and concentration of catalyst with respect to solvent is maintained in the range of 2 to 20 g/L.

17. Process as claimed in claim 1 wherein the magnesium to aluminum molar ratio of the solid base in the catalyst is maintained at 3.5 and concentration of the catalyst with respect to solvent is maintained in the range of 2 to 20 g/L.

18. Process as claimed in claim 1 wherein the magnesium to aluminum molar ratio of the solid base in the catalyst system is maintained at 3.5 and reaction pressure is maintained in the range of 20 to 90 kg/cm².

19. Process as claimed in claim 1 wherein the magnesium to aluminum molar ratio of the solid base in the catalyst is maintained at 2.0 and reaction temperature is maintained in the range of 50 to 300° C.

20. Process as claimed in claim 1 wherein the weight ratio of the metal complex to solid base is in the range of 1:35 to 1:70.

21. Process as claimed in claim 20 wherein magnesium to aluminum molar ratio of the solid base in the catalyst system is maintained in the range 1.5 to 3.5.

22. Process as claimed in claim 1 wherein n is in the range of 2 to 9.

23. Process as claimed in claim 21 wherein weight ratio of the metal complex to solid base in the catalyst system is maintained at 1:35 and magnesium to aluminum molar ratio of the solid base in the catalyst is maintained at 3.5.

24. Process as claimed in claim 15 where n is 3 and the weight ratio of metal complex to solid base in the catalyst system is maintained at 1:35 and magnesium to aluminum molar ratio of the solid base in the catalyst is maintained at 3.5.

25. Process as claimed in claim 15 where n is 6, the weight ratio of the metal complex to solid base in the catalyst system is maintained at 1:35 and the magnesium to aluminum molar ratio of the solid base in the catalyst is maintained at 3.5.

26. Process as claimed in claim 15 where n is 9, weight ratio of the metal complex to solid base in the catalyst system is 1:35 and the magnesium to aluminum molar ratio of the solid base in the catalyst is maintained at 3.5.

27. Process as claimed in claim 15 where n is 10, weight ratio of the metal complex to solid base in the catalyst system is 1:35 and the magnesium to aluminum molar ratio of the solid base in the catalyst is maintained at 3.5.

28. Process as claimed in claim 15 where n is 3, weight ratio of the metal complex to solid base in the catalyst system is 1:35, the magnesium to aluminum molar ratio of the solid base in the catalyst is 1.5 and concentration of the catalyst with respect to solvent is maintained in the range of 2 to 30 g/L.

29. Process as claimed in claim 15 where n is 3, weight ratio of metal complex to solid base in the catalyst is 1:35, the magnesium to aluminum molar ratio of the solid base in the catalyst is 1.5 and the temperature is maintained in the range of 80 to 250° C.

30. Process as claimed in claim 15 where n is 3 and the magnesium to aluminum molar ratio of the solid base is in the range of 2.0 to 3.5.

31. Process as claimed in claim 15 where n is 3 and the reaction temperature is maintained in the range of 50° C. to 300° C.

32. Process as claimed in claim 15 where n is 3 and the reaction pressure is maintained in the range of 20 to 90 kg/cm$^2$.

33. Process as claimed in claim 15 where n is in the range of 2 to 10 and the weight ratio of the metal complex and the solid base is in the range of 1:35 to 1:70.

34. Process as claimed in claim 15 where n is 3 and the magnesium to aluminum molar ratio in the solid base is selected from the group consisting of 1.5, 2.0, 2.5 and 3.5.

35. Process as claimed in claim 15 where n is 3 and 2 to 30 g/L of the catalyst system is used.

36. Process as claimed in claim 15 where n is 3 and the aldol reaction temperature is in the range of 80° C. to 250° C.

* * * * *